(12) United States Patent
Harino et al.

(10) Patent No.: US 6,238,385 B1
(45) Date of Patent: May 29, 2001

(54) LASER TREATMENT APPARATUS

(75) Inventors: Seiyo Harino, Osaka; Hirokazu Nakamura, Aichi; Seiki Tomita, Aichi; Yasuyuki Naito, Aichi; Toshifumi Sumiya, Aichi, all of (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/088,656

(22) Filed: Jun. 2, 1998

(30) Foreign Application Priority Data

Jun. 2, 1997 (JP) .................................................. 9-160622

(51) Int. Cl.$^7$ .......................................................... A61F 9/01
(52) U.S. Cl. ................................... 606/4; 606/10; 606/13
(58) Field of Search ............................... 606/2, 3, 6, 13; 351/206–211

(56) References Cited

U.S. PATENT DOCUMENTS

| | | | |
|---|---|---|---|
| 4,418,689 | * 12/1983 | Kanazawa | 606/15 |
| 4,917,486 | * 4/1990 | Raven et al. | 606/4 |
| 5,057,102 | * 10/1991 | Tomioka et al. | 606/4 |
| 5,098,426 | * 3/1992 | Sklar et al. | 606/4 |

FOREIGN PATENT DOCUMENTS

| | | |
|---|---|---|
| 0 279 589 A1 | 8/1988 | (EP) . |
| 0 293 126 A1 | 11/1988 | (EP) . |
| 0 446 044 A2 | 9/1991 | (EP) . |
| 0 724 858 A1 | 8/1996 | (EP) . |
| 2 716 367 | 8/1995 | (FR) . |
| 9-173351 | 7/1997 | (JP) .............................. A61B/19/00 |

\* cited by examiner

*Primary Examiner*—David M. Shay
(74) *Attorney, Agent, or Firm*—Sughrue, Mion, Zinn, Macpeak & Seas, PLLC (57) ABSTRACT

A laser treatment apparatus having a guide beam forming mechanism for guiding a treatment laser beam to a diseased part, including a laser beam irradiation optical system which irradiates the diseased part with the treatment laser beam, a target for obtaining a position of the central fovea of a patient's eye which is projected to the fundus, and a fixation mark for fixing the patient's eye so that the central fovea is located at a predetermined position with respect to the target. With the laser treatment apparatus, the central fovea of a patient's eye is easily judged, and, even for a patient's eye having reduced central visual acuity, the fixation is stably conducted.

13 Claims, 7 Drawing Sheets

LASER TREATMENT APPARATUS

BACKGROUND OF THE INVENTION

The invention relates to a laser treatment apparatus which irradiates a diseased part of a patient's eye with a treatment laser beam, thereby treating the diseased part of the patient's eye by means of photocoagulation or the like.

In order to treat a para fovea neovascularization formed in the vicinity of the central fovea and due to a disease in which the main lesion is choroidal neovascularization, such as age related macular degeneration, the laser treatment wherein the diseased part is irradiated with a laser beam so that the diseased part is photocoagulated is mainly employed. In this treatment, it is very important to determine the position of the central fovea so as not to affect the central fovea.

Conventionally, the position of the central fovea is determined while fixing the patient's eye to an aiming beam having a circular shape of about 50 $\mu$m. Alternatively, the position of the central fovea is determined in the following manner. After an eye is fixed to an external fixation lamp attached to a slit lamp or the like, an aiming beam is moved (scanned) vertically and horizontally, and it is checked whether the aiming beam can be visually recognized or not.

However, the former method in which an eye is fixed to an aiming beam has a problem in that, since the spot size of the aiming beam is as small as about 50 $\mu$m, an eye of a patient having reduced central visual acuity is unstably fixed to the beam, and hence the aiming beam is moved when the laser irradiation is conducted.

In the latter method, skill is required to correctly determine the position of the central fovea, and therefore it is often difficult to determine the position of the central fovea.

SUMMARY OF THE INVENTION

The invention has been made in view of the above-discussed problems. It is an object of the invention to provide a laser treatment apparatus in which the fixation of a patient's eye can be stabilized, the operator can correctly know the position of the central fovea of the patient's eye, and treat (photocoagulate) the diseased part near the central fovea safely.

In order to solve the problems, the invention is characterized in the following configuration.

(1) A laser treatment apparatus comprising a guide beam forming means for guiding a treatment laser beam to a diseased part,
- a laser beam irradiation optical system which irradiates the diseased part with the treatment laser beam is characterized in that the apparatus further comprises: an illumination optical system which illuminates an fundus of a patient's eye; an observation optical system through which the fundus of the patient's eye is observed; a target projection optical system which projects a target for obtaining a position of a central fovea of the patient's eye, to the fundus; and a fixation mark projection optical system which projects a fixation mark for fixing the patient's eye so that the central fovea is located at a predetermined position with respect to the target.

(2) The apparatus is characterized in that the target projection optical system of (1) is used also as the fixation mark projection optical system.

(3) In the laser treatment apparatus of (1), it is characterized in that the target is a cross chart and has a size specifying a region which does not affect the central fovea in laser irradiation to the fundus.

(4) In the laser treatment apparatus of (3), it is characterized in that the target has a size which can be visually recognized by a region of a retina of a patient's eye in which a central fovea is disturbed, the region not being disturbed.

(5) In the laser treatment apparatus of (3), it is characterized in that a scale for specifying a distance is formed in the cross chart.

(6) In the laser treatment apparatus of (3), it is characterized in that a concentric circular mark, or a matrix-like grid line is attached to the cross chart.

(7) In the laser treatment apparatus of (1), it is characterized in that the target projection optical system and the fixation mark projection optical system share a part of an optical path of the illumination optical system or the observation optical system.

(8) In the laser treatment apparatus of (7), it is characterized in that the apparatus further comprises attaching and detaching means for allowing the target projection optical system and the fixation mark projection optical system to be attached to and detached from the illumination optical system or the observation optical system.

(9) In the laser treatment apparatus of (1), it is characterized in that the apparatus further comprises variable magnifying means for varying a size of an image of the mark projected by the fixation mark projection optical system.

(10) In the laser treatment apparatus of (1), it is characterized in that the apparatus further comprises a slit lamp microscope, a surgical microscope, or a fundus camera.

(11) In the laser treatment apparatus of (1), it is characterized in that a color of the target projected by the target projection optical system is different from a color of an aiming beam.

(12) In the laser treatment apparatus of (1), it is characterized in that the apparatus further comprises changing means for changing a color of the target projected by the target projection optical system.

(13) In the laser treatment apparatus of (1), it is characterized in that the apparatus further comprises moving means for moving a position of an image of the target projected by the target projection optical system, on the fundus.

(14) A laser treatment apparatus comprising a guide beam forming means for guiding a treatment laser beam to a diseased part,
- a laser beam irradiation optical system which irradiates the diseased part with the treatment laser beam is characterized in that the apparatus further comprises: an illumination optical system which illuminates an fundus of a patient's eye; an observation optical system through which the fundus of the patient's eye is observed; and a target projection optical system which projects a target for fixing the patient's eye, and for obtaining a position of a central fovea of the patient's eye, to the fundus.

DETAILED DESCRIPTION OF THE PREFERRED EMBODIMENT

Figure 1:
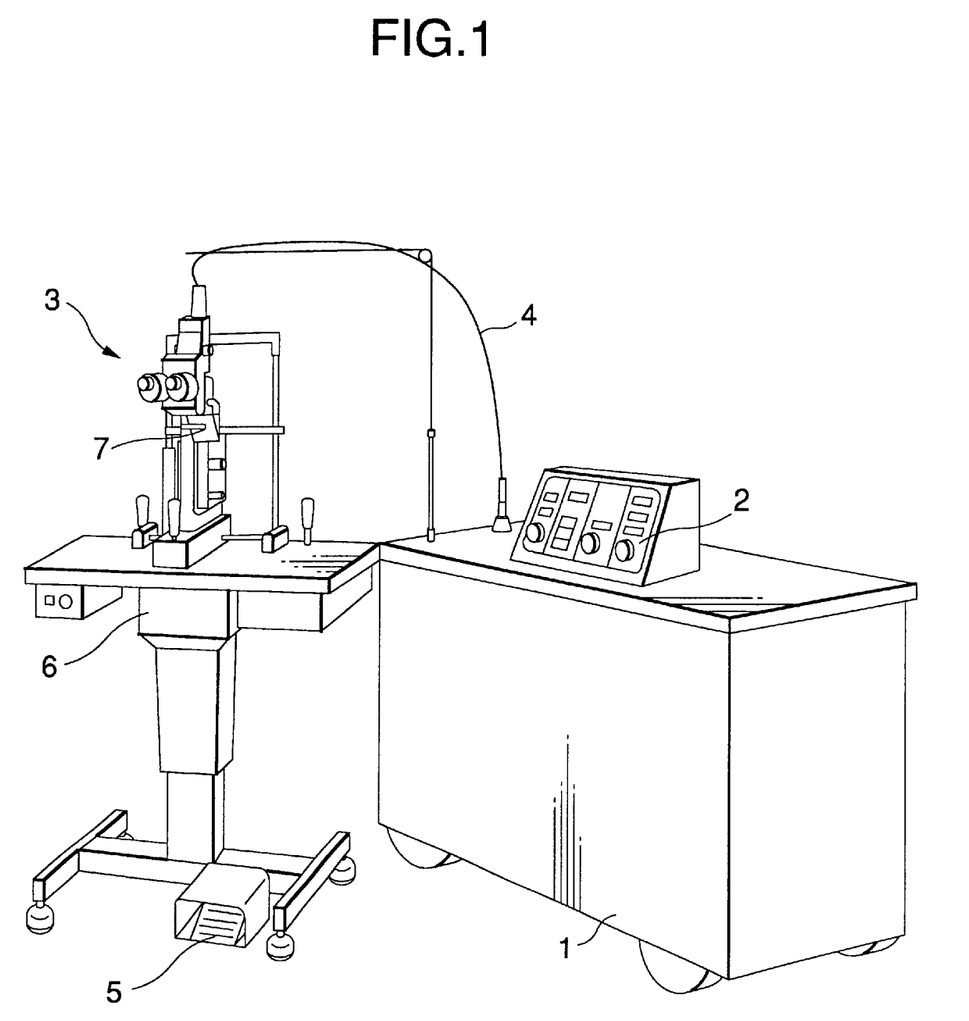
FIG. 1 is an external diagrammatic view of a laser treatment apparatus which is an embodiment.

Hereinafter, the invention will be described with reference to the accompanying drawings. FIG. 1 is an external diagrammatic view of a laser treatment apparatus which is an embodiment.

The reference numeral 1 designates the body of a laser apparatus which houses a light source of a treatment laser beam, a light source of an aiming beam, a control section, etc. As the treatment laser beam, an argon laser, a krypton laser, a dye laser, and the like may be used. The reference numeral 2 designates a control unit through which conditions of the laser irradiation output, such as a laser output level and an irradiation time are set and input, 3 designates a slit lamp delivery device comprising an illumination optical system 10, an observation optical system 30, and an irradiation optical system 40 which irradiates a diseased part of a patient's eye with the laser beam, and 4 designates an optical fiber cable. The treatment laser beam and the aiming beam which are oscillated in the laser apparatus body 1 are delivered to the irradiation optical system 40 of the slit lamp delivery device 3 through the optical fiber cable 4.

The reference numeral 5 designates a foot switch for outputting a trigger signal for laser irradiation, 6 designates a pedestal for vertically moving the slit lamp delivery device 3, and 7 designates a manipulator for driving a driven mirror 44 that will be described later.

Figure 2:
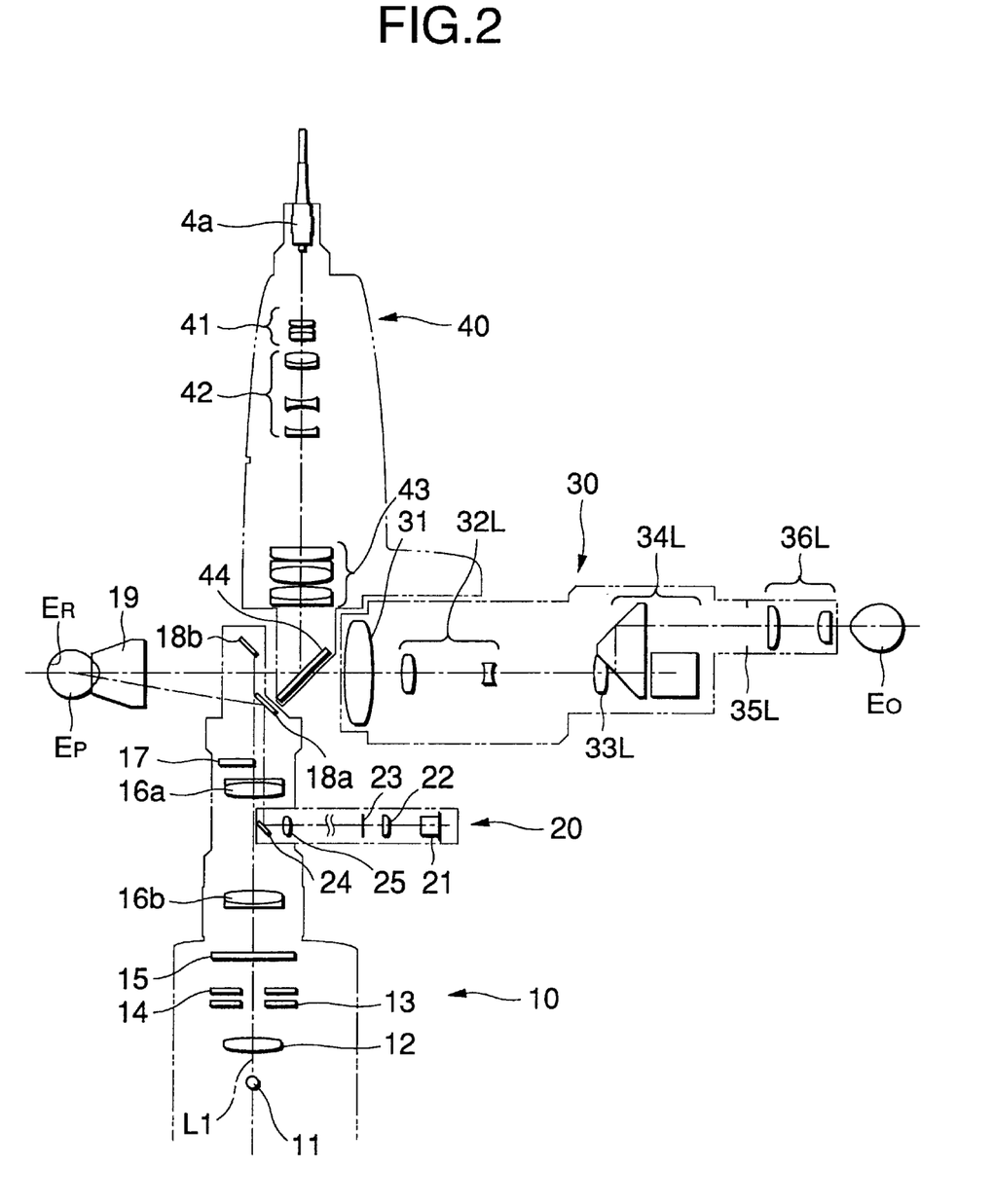
FIG. 2 is a side view of main portions of an optical system of a slit lamp delivery device.
Figure 3:
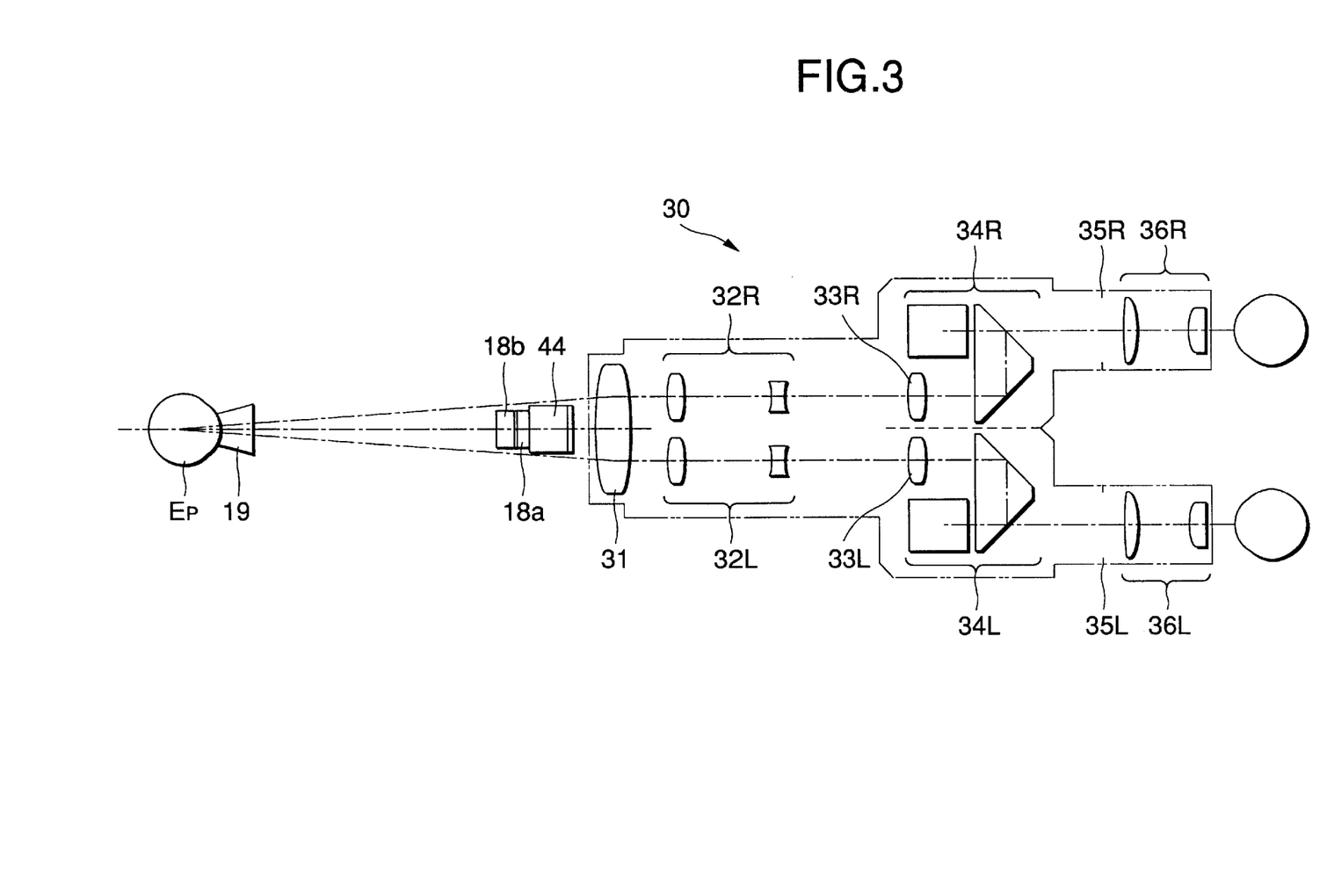
FIG. 3 is a plan view of the main portions of the optical system of the slit lamp delivery device.

FIG. 2 is a side view of main portions of an optical system of the slit lamp delivery device 3, and FIG. 3 is a plan view of the main portions.

The reference numeral 10 designates the illumination optical system. The reference numeral 11 designates an illumination light source which emits visible light, 12 designates a condenser lens, 13 designates a variable circular aperture in which the aperture diameter is variable, 14 designates a variable slit plate in which the slit width is variable, 15 designates a filter, 16a and 16b designate projection lenses, 17 designates a correcting lens, and 18a and 18b designate split mirrors. In the embodiment, a (tungsten) halogen lamp is used as the illumination light source 11. The visible light flux emitted from the illumination light source 11 is transmitted through the condenser lens 12. Thereafter, the height of the light flux is defined by the variable circular aperture 13, and the width of the light flux is defined by the variable slit plate 14, so that the light flux is formed into a slit-like light flux. Thereafter, the light flux which is on the side of the operator's eye $E_O$ with respect to the illumination optical axis $L_1$ is directed to the split mirror 18a through the filter 15 and the projection lenses 16a and 16b. The light flux which is on the side of the patient's eye $E_P$ with respect to the illumination optical axis $L_1$ is subjected to the correction of the optical path length by the correcting lens 17 and then directed to the split mirror 18b. The slit light fluxes reflected from the split mirrors 18a and 18b impinge (illuminate) on the fundus of the patient's eye through a contact lens 19.

The reference numeral 20 designates a (target) mark projection optical system. The reference numeral 21 designates a light source for mark projection. In the embodiment, a semiconductor laser device which emits red light of a wavelength of 635 nm is used as the light source. The reference numeral 22 designates a collimator lens, 23 designates a target plate, 24 designates a mirror, and 25 designates a mark projection lens. A light beam emitted from the mark projection light source 21 passes through the collimator lens 22, the target plate 23, the mark projection lens 25, the mirror 24, and the projection lenses 16a, and is then reflected by the split mirror 18a, thereby projecting a target mark formed on the target plate 23 to the fundus region $E_R$ of the patient's eye.

Figure 4:
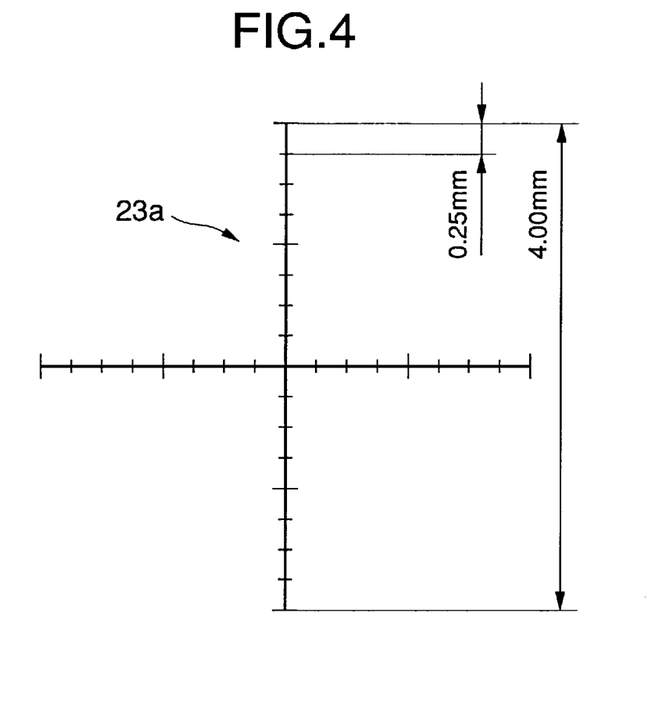
FIG. 4 is a view showing in detail an image of a target mark formed in a target plate.
Figure 8:
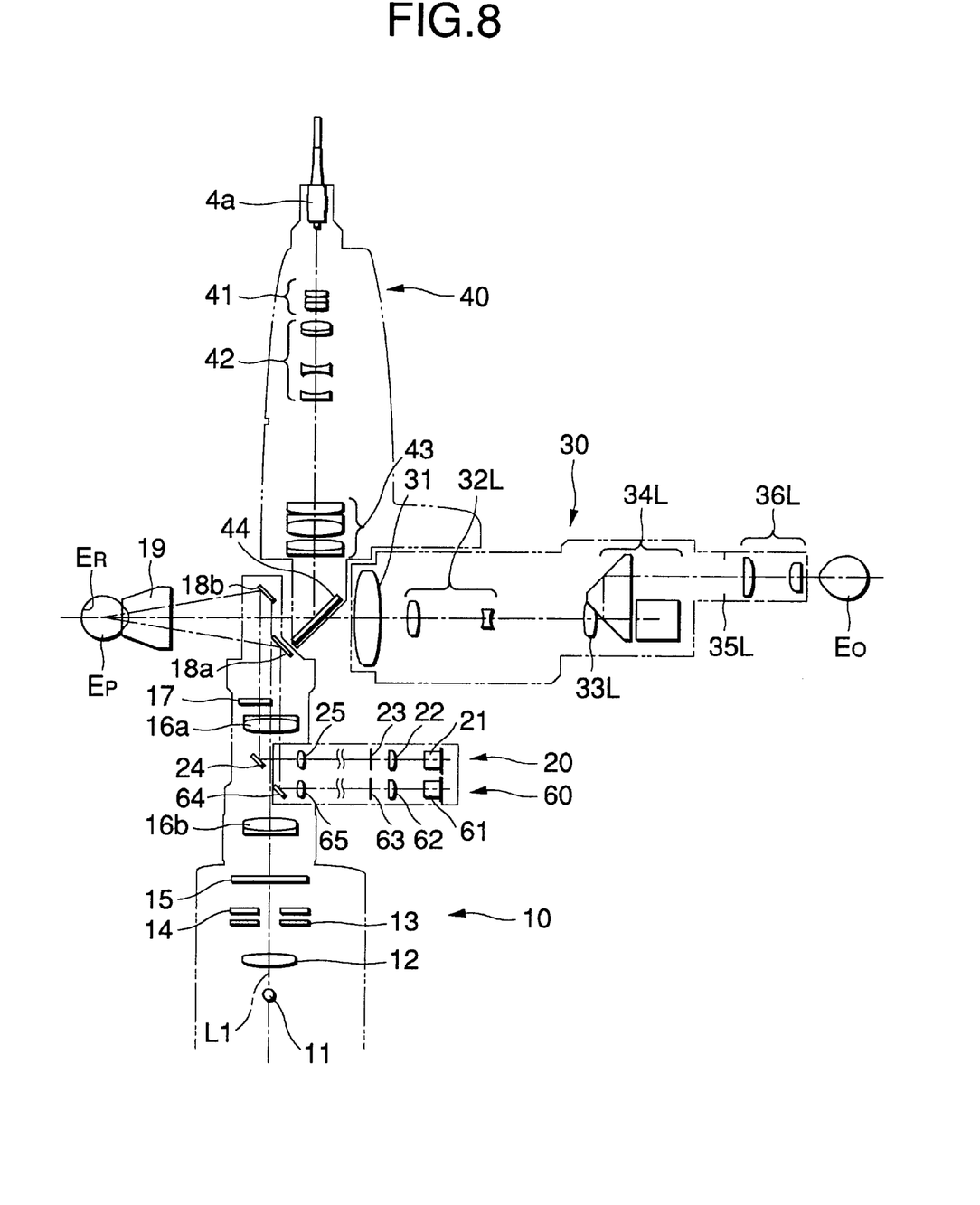
FIG. 8 is a side view showing a modified form of the main portions of the optical system of the slit lamp delivery device.

FIG. 4 is a view showing the shape of the target mark 23a formed on the target plate 23. In the embodiment, a cross chart is used as the target mark 23a, and a scale is formed on the cross hairs. The target mark 23a is formed so that the whole of the cross chart has a size of 4 mm×4 mm and ticks are arranged at intervals of 0.25 mm. The mark is projected to the fundus by the optical system. In the embodiment, a visible light source is used as the mark projection light source 21. Therefore, the target mark 23a can be visually recognized by the patient's eye and functions also as a fixation mark. Alternatively, in addition to the (target) mark projection optical system 20, a fixation target projection optical system 60 can be provided (see FIG. 8). A light beam emitted from a fixation target projection light source 61 passes through a collimator lens 62, a fixation target plate 63, a fixation target projection lens 65, a mirror 64, and the projection lens 16a, and is then reflected by the split mirror 18a, thereby projecting a fixation target formed on the fixation target plate 63 to the fundus region $E_R$ of the patient's eye. In this case, the light beam passed through the (target) mark projection optical system 20, the projection lens 16a and the correcting lens 17 is reflected by the split mirror 18b, thereby projecting the target mark formed on the target plate 23 to the fundus region $E_R$ of the patient's eye.

The reference numeral 30 designates the observation optical system. The reference numeral 31 designates an objective lens. A pair of left and right variable magnification lenses 32L and 32R, imaging lenses 33L and 33R, erecting prisms 34L and 34R, and field diaphragms 35L and 35R are arranged behind the objective lens 31. The operator observes an intermediate image formed in the field diaphragms 35L and 35R, through eyepiece lenses 36L and 36R.

The reference numeral 40 designates the laser irradiation optical system which irradiates the patient's eye with the laser beam (and the aiming beam) delivered by the optical fiber cable 4. The reference numeral 41 designates a collimator lens, 42 designates a variable magnification lens for changing the spot size of the laser beam, 43 designates an objective lens, and 44 designates the driven mirror. The operator operates the manipulator 7 so as to drive the driven mirror 44, thereby moving the spot position of the laser beam independently of the projected image of the mark. As shown in FIG. 3, the observation optical system 30 is a binocular observation system. Consequently, the driven mirror 44 is disposed without obstructing the left and right observation optical axes. A dichroic mirror which reflects the laser beam and the aiming beam and allows an observation illumination light beam to pass therethrough may be used in place of the driven mirror 44.

The treatment laser beam which is oscillated in the laser apparatus body 1 passes through the optical fiber cable 4 and enters the irradiation optical system 40 from the emerging end 4a of the optical fiber cable 4. The laser beam flux which enters the irradiation optical system 40 passes through the collimator lens 41, the variable magnification lens 42, and the objective lens 43, and is then reflected by the driven mirror 44 to be delivered to a diseased part of the fundus of the patient's eye.

Figure 6A:
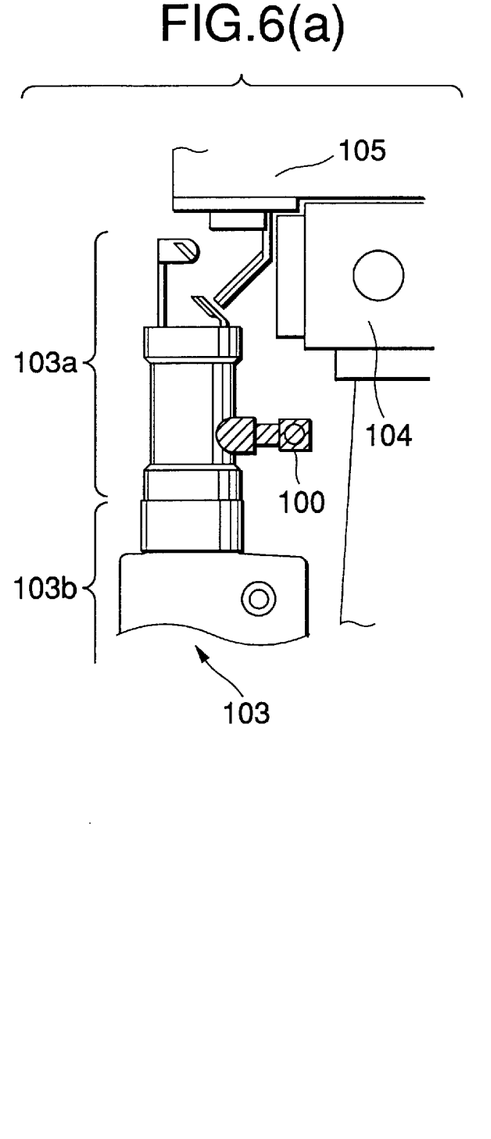
FIGS. 6(a) and 6(b) are external diagrammatic views showing a case in the vicinity of the optical system to which a mark projection optical system is attached, and a power source for a light source for mark projection.
Figure 6B:
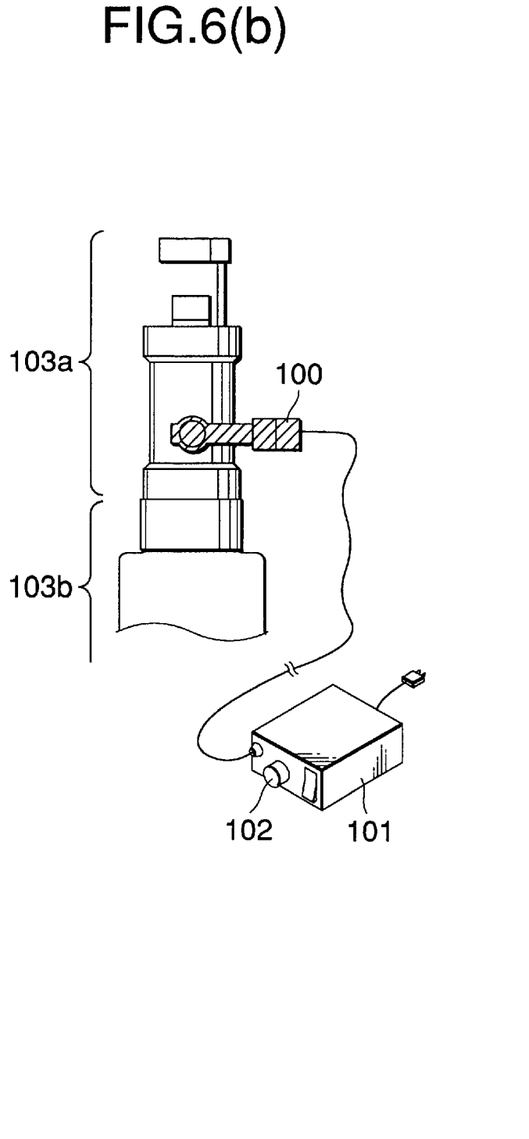

FIGS. 6(a) and 6(b) are external diagrammatic views showing a case which houses the mark projection optical system 20, and the vicinity of the case. FIG. 6(a) is a side view, and FIG. 6(b) is a front view. The hatched portion 100 is the mark projection system case which houses the mark projection optical system 20. A power source unit 101 for the mark projection light source 21 is connected to the mark projection system case 100. The power source unit 101 is provided with an adjusting knob 102. The brightness of the mark projection light source 21 can be adjusted by operating the adjusting knob 102. The reference numeral 103 designates an illumination system case which houses the illumination optical system 10, 104 designates an observation system case which houses the observation optical system 30, and 105 designates an irradiation system case which houses the laser irradiation optical system 40.

In the embodiment, the illumination system case 103 is configured by a split mirror head portion 103a and a base portion 103b. The split mirror head portion 103a can be attached to and detached from the base portion 103b by means of screwing. The mark projection system case 100 is fixed to the split mirror head portion 103a. When the split mirror head portion 103a is replaced with a usual one, therefore, the system may be used as a slit illumination system.

The illumination system case 103 is rotatable with respect to the observation system case 104, so that the patient's eye can be illuminated from a direction desired by the observer.

Next, the operation of the thus configured apparatus in the case of photocoagulation against age related macular degeneration will be described.

The operator operates the control unit 2 to set coagulation conditions such as the laser output level and the irradiation time. When the laser apparatus body 1 is ready for laser irradiation, the light sources of the illumination optical system 10 and the mark projection optical system 20 are turned on. Thereafter, a joy stick is operated so as to move the slit lamp delivery device 3, and the fundus of the patient's eye is observed while illuminating the fundus. When the fundus of the patient's eye is illuminated, an image of the cross chart (the target mark 23a) which is coaxial with the illumination system is projected. The image of the cross chart is formed on the retina (the eyeground fundus $E_R$ of the patient's eye), and hence the patient can visually recognize the cross chart. The operator instructs the patient to look at the center of the cross chart so as to attain the fixation.

The size of the projected image of the cross chart is wider than that of the spot of an aiming beam used in the prior art. Even for a patient having reduced central visual acuity, therefore, the fixation can be attained in a relatively satisfactory manner. The configuration in which the fixation mark is a cross chart enables even a patient's eye in which, for example, the macular lutea is disturbed and which can not visually recognize a center portion of the cross chart, to recognize the cross chart (estimate the center portion of the cross chart) because the four end portions of the mark impinge on the normal retina. Consequently, the eye can be fixed to the mark. Furthermore, a diaphragm may be disposed in the optical path dedicated to the mark projection optical system 20 so that the vertical and horizontal lines of the image of the cross chart can be changed in length. According to this configuration, the image of the cross chart can be visually recognized even by a patient who cannot visually recognize a cross chart of a usual size.

Figure 5:
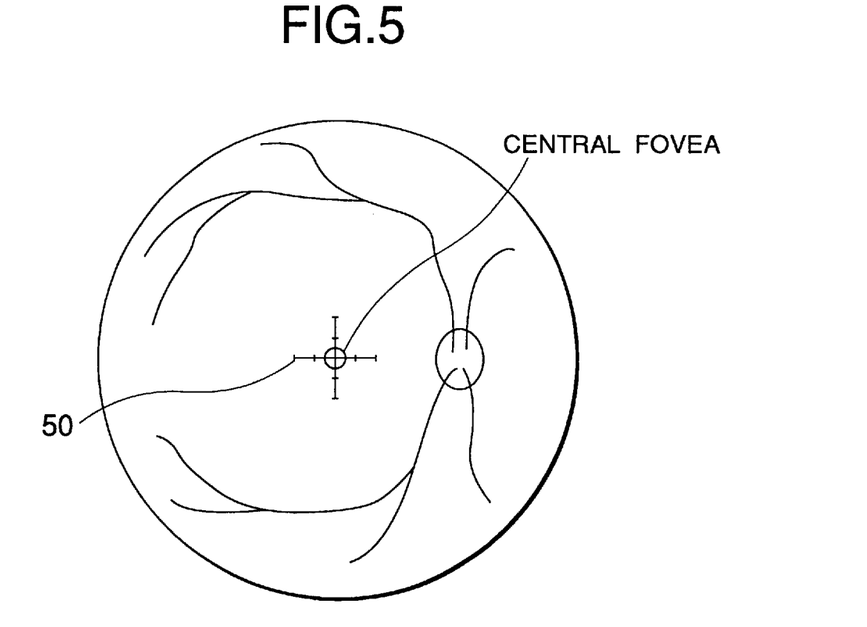
FIG. 5 is a view showing an example of a target image projected to an eyeground.

Since the target image such as shown in FIG. 5 is projected to the fundus of the patient's eye, the operator observes the projected image. As a result of the fixation of the patient's eye, the center of the image 50 of the target mark which is projected to the fundus region $E_R$ of the patient's eye substantially corresponds to the central pit of the central fovea (the hatched portion). Therefore, the operator can correctly know the position of the central fovea. Since the scale is formed in the image of the cross chart, the operator can recognize the size of the region where the effect due to the laser irradiation centered at the central pit occurs with a high probability, and thus the treatment can be appropriately performed based on this recognition.

After the region to be treated is recognized, the operator operates the manipulator 7 while the patient continues the fixation to the image of the cross chart, so that the aiming beam of the laser irradiation optical system 40 is aimed at the region to be treated (para fovea neovascularization), and the spot size, and the like are adjusted. When the aiming operation is completed, photocoagulation is started by pressing the foot switch 5.

The trigger signal from the foot switch 5 is transmitted to the control section (not shown) disposed in the laser apparatus body 1. The control section causes the treatment laser beam to be oscillated under the set conditions which are previously input to the control unit 2. The treatment laser beam passes the same optical path as that of the aiming beam and then impinges on the diseased part, thereby performing the photocoagulation treatment.

Figure 7A:
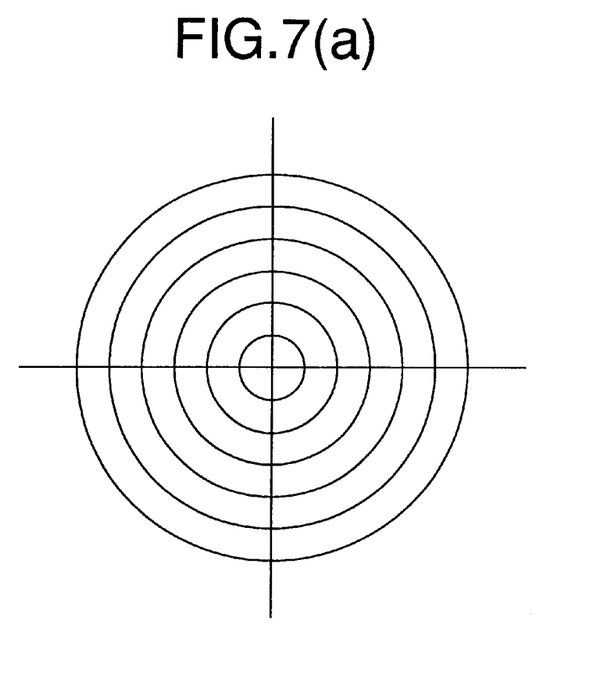
FIGS. 7(a) and 7(b) are views showing modifications of the target mark.
Figure 7B:
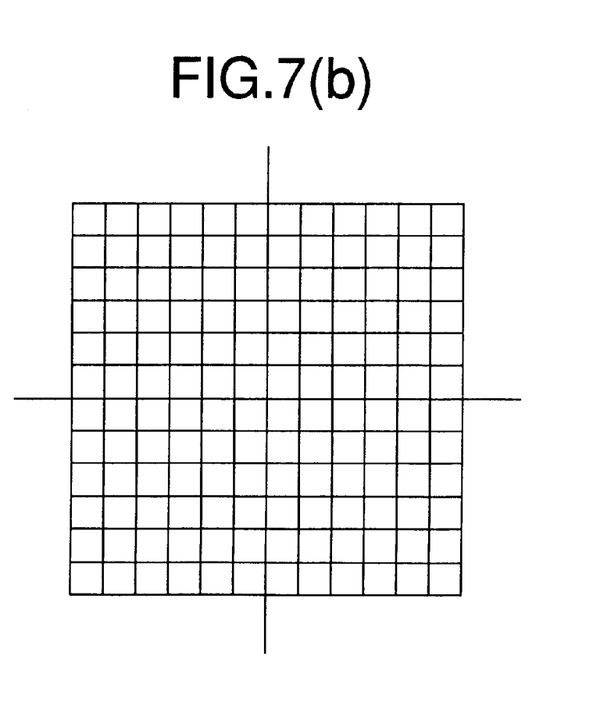

In the embodiment described above, the target mark 23a is formed as a cross chart and the scale is formed on the cross hairs. Alternatively, concentric circular marks may be added to the cross chart (see FIG. 7(a)), or a mark having a matrix-like shape formed by grid lines (see FIG. 7(b)) may be used. In the alternative, the ring-like marks or the grid lines can be used in place of the scale. When such a target mark is used, it is possible to know the surface configuration of the central fovea, and hence the treatment can be performed more appropriately.

When the target mark which is to be projected to the fundus is formed so as to be movable, the guidance of the fixation can be appropriately conducted in accordance with the kind of the treatment. For example, the target mark may be moved in the following manner. The mirror 24 of the mark projection optical system 20 is configured so as to be driven in the same manner as the driven mirror 44, and the driving is conducted by operating a manipulator, thereby moving the target mark. Alternatively, since a mirror for changing the optical path is disposed in the mark projection system case 100 in addition to the mirror 24, knobs for operating the two mirrors so as to be independently tilted may be disposed.

In the embodiment, the semiconductor laser device which emits red light of a wavelength of 635 nm is used as the light source for projection of the mark. Alternatively, a light source of another kind such as an LED may be used as far as it can produce a required amount of light. The useful wavelength is not restricted to red light, and various kinds of visible light such as yellow, orange, or green may be used. In order to allow the operator to distinguish the mark images from each other in the observation, preferably, the light source for aiming, and that for target projection have different wavelengths (colors). Plural light sources emitting light beams of different colors such as red and green may be interchangeably disposed, or the color of the light source may be selected by switching means.

The slit lamp delivery device has been described as the embodiment. Alternatively, the embodiment may be used in various kinds of microscopes such as a surgical microscope, or may be used in combination with a fundus camera.

The case in which the mark projection optical system is connected to the illumination optical system has been described. Alternatively, the mark projection optical system may be disposed in the observation optical system or other optical system, such that light is caused to impinge on the fundus of the patient's eye after the optical axis of the mark projection optical system is made coincident with the optical axis of the optical system in which the mark projection optical system is disposed.

As described above, according to the preferred embodiment of the invention, the central fovea of a patient's eye can be easily judged, and, even for a patient's eye having reduced central visual acuity, the fixation can be stably conducted.

What is claimed is:

1. A laser treatment apparatus for coagulating a diseased part of a fundus of a patient's eye with a treatment laser beam, the treatment laser beam being guided to the diseased part using an aiming beam, the apparatus comprising:
    a laser beam irradiation optical system which irradiates the diseased part with the treatment laser beam;
    an illumination optical system which illuminates the fundus of the patient's eye;
    an observation optical system through which the fundus is observed; and
    a target projection optical system which projects a target of a two dimensional shape having a center and indicating a distance from the center, and which forms an image of the target on the fundus;
    wherein fixation of the patient's eye at the center of the target causes a center of the target image to be positioned at a central fovea of the fundus; and
    wherein an optical path of the target projection optical system is located at a position that is not influenced by a driven mirror disposed in the laser beam irradiation optical system.

2. A laser treatment apparatus according to claim 1, further comprising:
    moving means for moving a position of the target image on the fundus.

3. A laser treatment apparatus according to claim 1, further comprising:
    changing means for changing a color of the target.

4. A laser treatment apparatus according to claim 1, wherein a color of the target is different from a color of the aiming beam.

5. A laser treatment apparatus according to claim 1, further comprising a slit lamp microscope including the illumination optical system and the observation optical system.

6. A laser treatment apparatus according to claim 1, further comprising:
    variable magnifying means for varying a size of the target image.

7. A laser treatment apparatus according to claim 1, further comprising a fixation target projection optical system which projects a fixation target so as to overlap the center of the target.

8. A laser treatment apparatus according to claim 1, wherein the target has a size utilized for confirming a region to which the treatment laser beam can be irradiated so as not to affect the central fovea.

9. A laser treatment apparatus according to claim 1, wherein the target has a size which can be visually recognized by a region of a retina of a patient's eye in which a central fovea is diseased, the region not being diseased.

10. A laser treatment apparatus according to claim 1, wherein the target has a scale for specifying the distance from the center.

11. A laser treatment apparatus according to claim 1, wherein the target includes at least one of a cross chart target, a concentric circular mark target and a matrix-like grid line target.

12. A laser treatment apparatus according to claim 1, wherein a part of the optical path of the target projection optical system is shared with a part of an optical path of the illumination optical system or a part of an optical path of the observation optical system.

13. A laser treatment apparatus according to claim 12, wherein the part of the optical path of the target projection optical system is attached to and detached from the part of the optical path of the illumination optical system or the part of the optical path of the observation optical system.

* * * * *